(12) United States Patent
Oliveira et al.

(10) Patent No.: US 11,990,232 B2
(45) Date of Patent: May 21, 2024

(54) CLINICAL DISCOVERY WHEEL—A SYSTEM TO EXPLORE CLINICAL CONCEPTS

(71) Applicant: KONINKLIJKE PHILIPS N.V., Eindhoven (NL)

(72) Inventors: Lucas de Melo Oliveira, Melrose, MA (US); Douglas Henrique Teodoro, Sao Paulo (BR); Yuechen Qian, Lexington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 212 days.

(21) Appl. No.: 15/776,465

(22) PCT Filed: Nov. 22, 2016

(86) PCT No.: PCT/IB2016/057019
§ 371 (c)(1),
(2) Date: May 16, 2018

(87) PCT Pub. No.: WO2017/093846
PCT Pub. Date: Jun. 8, 2017

(65) Prior Publication Data
US 2018/0330807 A1 Nov. 15, 2018

Related U.S. Application Data

(60) Provisional application No. 62/260,687, filed on Nov. 30, 2015.

(51) Int. Cl.
*G16H 40/63* (2018.01)

(52) U.S. Cl.
CPC ................... *G16H 40/63* (2018.01)

(58) Field of Classification Search
CPC ........ G16H 40/63; G16H 10/60; G16H 50/20; G16H 40/20; G16H 80/00; G16H 40/67;
(Continued)

(56) References Cited

U.S. PATENT DOCUMENTS

| 8,521,561 B2 | 8/2013 | Sasai et al. |
| 8,830,270 B2 | 9/2014 | Zaman et al. |

(Continued)

FOREIGN PATENT DOCUMENTS

| CN | 102331932 A | 1/2012 |
| JP | 2013536503 A | 9/2013 |

(Continued)

OTHER PUBLICATIONS

"Mapping of IFCC-IUPAC Laboratory Coding System to Snomed CT" Chemistry International—Newsmagazine for IUPAC, vol. 29, No. 2, 2007, pp. 18-18. https://doi.org/10.1515/ci.2007.29.2.18b (Year: 2007).*

*Primary Examiner* — Michael Tomaszewski
*Assistant Examiner* — Shyam M Goswami (57) ABSTRACT

The following relates to an improved system and method for displaying medical information. In one aspect, a root concepts circle including at least one clinical concept category is displayed. A children concept ring, which may be built based on a user-selected clinical concept category of the at least one clinical concept categories, may surround or partially surround the root concept circle. A ring fashion timeline may also be displayed, and may be built based on a user-selected clinical concept of the at least one clinical concepts.

13 Claims, 5 Drawing Sheets

(58) Field of Classification Search
CPC ........ G16H 50/30; G16H 20/00; G16H 20/40;
G16H 40/40; H04L 67/10; H04L 29/08;
H04L 12/24; G06F 19/30; G06F 19/32;
G06F 19/34; G06F 19/36; G06F 3/0484;
G06F 19/00; G06Q 50/22; G06Q 50/24;
A61B 5/00; A61B 5/145; A61B 5/14552;
A61B 5/02; A61B 5/14542; A61B
5/7475; A61B 5/742; A61B 5/14546;
A61B 5/01; A61B 5/0022; A61B 5/746;
A61B 2560/0271; A61B 5/4848; A61B
2017/00809
See application file for complete search history.

(56) References Cited

U.S. PATENT DOCUMENTS

| | | |
|---|---|---|
| 2005/0222873 A1 | 10/2005 | Nephin et al. |
| 2006/0161863 A1 | 7/2006 | Gallo |
| 2008/0052126 A1* | 2/2008 | Sasai ............ G16H 15/00 705/3 |
| 2009/0299645 A1* | 12/2009 | Colby ............ C12Q 1/6886 702/19 |
| 2010/0198612 A1* | 8/2010 | Streepy, Jr. ...... G16H 70/60 707/769 |
| 2011/0033093 A1 | 2/2011 | Salz et al. |
| 2011/0087624 A1 | 4/2011 | Hale et al. |
| 2012/0060216 A1 | 3/2012 | Chaudhri et al. |
| 2014/0038063 A1 | 2/2014 | Saito et al. |
| 2014/0149407 A1 | 5/2014 | Qian et al. |
| 2014/0184608 A1* | 7/2014 | Robb ............ A61B 6/5217 345/440 |
| 2015/0058769 A1 | 2/2015 | Kim |

FOREIGN PATENT DOCUMENTS

| | | |
|---|---|---|
| JP | 2015179319 A | 10/2015 |
| WO | 2012017418 A1 | 2/2012 |

* cited by examiner

CLINICAL DISCOVERY WHEEL—A SYSTEM TO EXPLORE CLINICAL CONCEPTS

CROSS-REFERENCE TO PRIOR APPLICATIONS

This application is the U.S. National Phase application under 35 U.S.C. § 371 of International Application No. PCT/IB2016/057019, filed on Nov. 22, 2016, which claims the benefit of U.S. Provisional Application Ser. No. 62/260,687, filed Nov. 30, 2015. These applications are hereby incorporated by reference herein, for all purposes.

BACKGROUND

The following relates to an improved system and method for navigating and displaying medical information.

Freeform medical reports are produced in various clinical domains. In particular, radiology examinations are summarized in freeform reports prepared by radiologists. A radiology examination is ordered and usually has a "reason for examination" included in the order. However, in practice the radiologist report may address other clinical conditions besides the stated reason for examination. Likewise, the freeform radiology reports may include content relating to numerous clinical concept categories, such as clinical findings, symptoms, diagnoses, procedures, or anatomical structures. These freeform medical reports are thus a source of significant information for medical personnel evaluating a patient, especially one who has multiple chronic or acute ailments. However, the freeform nature of these reports make it difficult to extract useful information.

One way of addressing this problem might be to use structured report forms with no freeform text entry fields. However, such structured reporting would significantly constrain the radiologist or other medical professional, possibly resulting in an inability to enter key finding which do not "fit into" the pre-selected structured report form, or requiring entry of such findings in a way that does not fully capture the author's intended meaning. Such constraints are particularly likely in situations in which the author identifies findings relating to subject matter well outside of the scope of the original reason for examination.

In addition, the adoption of healthcare informatics systems such as Electronic Medical Record (EMR) and Radiology Information System (RIS) has allowed radiologists and referring physicians to have access to an enormous amount of patient data. Unfortunately, these data are spread across different healthcare databases. Therefore, to access relevant patient data, radiologists and referring physicians must spend a significant amount of time navigating different parts of different healthcare systems simply to learn patient information. This counterproductive task is workflow disruptive, and limits the full utilization of patient data stored in this healthcare ecosystem.

The following provides a new and improved systems and methods which overcome the above-referenced problems and others.

SUMMARY

In one aspect, a non-transitory storage medium storing instructions readable and executable by an electronic device to perform a method for navigating clinical information using a wheel structure in a graphical user interface is presented. The method includes: annotating medical reports by associating clinical concepts with text segments of the medical reports; building and displaying on a display device a root concepts ring or arc including arc segments representing clinical concept categories; receiving via a user input device operating on the displayed root concepts ring or arc a user selection of an arc segment representing a clinical concept category whereby a user-selected clinical concept category is identified; building and displaying a children concept ring or arc expanding the user-selected clinical concept category and at least partially encircling the root concepts ring or arc, the children concept ring or arc including arc segments representing clinical concepts of the user-selected clinical concept category; receiving via the user input device operating on the displayed children concept ring or arc a user selection of an arc segment representing a clinical concept whereby a user-selected clinical concept is identified; and building and displaying, adjacent the children concept ring or arc, a timeline comprising arc segments or blocks representing medical reports annotated with the user-selected clinical concept.

In another aspect, an electronic device for displaying medical information including building a root region and outwardly expanding regions is presented, the electronic device includes: a display device; a user input device; and an electronic processor programmed to: build and display on the display device a root region including icons representing clinical concept categories; build and display on the display device a first outwardly expanding region at least partially surrounding the root region and including icons representing clinical concepts of a user-selected clinical concept category selected via the user input device from the root region; and build and display on the display device a second outwardly expanding region including icons representing clinical concepts or medical reports of a user-selected clinical concept selected via the user input device from the first outwardly expanding region.

One advantage resides in a compact display for displaying medical information.

Another advantage resides in a reduced burden on processors and memory of a medical display device.

Another advantage resides in promoting continual awareness different viewing options in a medical display.

Another advantage resides in a more complete utilization of information available for a specific patient.

Another advantage resides in efficiently extracting and presenting information from diverse freeform textual sources.

Another advantage resides allowing for a quick clinical overview of a patient before beginning examination of an imaging study.

Other advantages will become apparent to one of ordinary skill in the art upon reading and understanding this disclosure. It is to be understood that a specific embodiment may attain, none, one, two, more, or all of these advantages.

The invention may take form in various components and arrangements of components, and in various steps and arrangements of steps. The drawings are only for purposes of illustrating the preferred embodiments and are not to be construed as limiting the invention.

DETAILED DESCRIPTION

A radiology workflow usually starts with a physician (usually called a referring physician) ordering an imaging study to investigate a clinical condition of a patient. In this order, the referring physician states the "reason of exam" and image modality using a paper or electronic request system. The imaging study is performed by a technician, and results in a series of images. In a subsequent reading of the imaging study, a radiologist investigates different images in the series of images with the goals of making one or more clinical findings (e.g., identifying a pulmonary nodule in the lung, or a suspicious mass in the liver, characterizing such features as potentially malignant, or so forth). The radiologist may also provide an appropriate treatment recommendation through a radiology report, although the referring physician more typically determines the treatment based on the radiology results and other available information. The referring physician will then read the radiology report and take appropriate action, for example prescribing further tests, a therapy regimen, or so forth. During these processes, radiologists and referring physicians may need to consult additional patient information to understand the clinical condition of the patient or to understand various details of the report information.

The approaches described herein facilitate exploring clinical concepts. One approach involves constructing and displaying a set of concentric circles via which users drive the discovery of processed patient information. This context-sensitive tool, described herein as the Clinical Discovery Wheel (CDW), uses a data-driven strategy to present relevant patient information providing a gradual exposure of information based on the user inputs. The CDW also may provide a longitudinal view of a selected clinical concept creating an interactive timeline wherein the progression of a given clinical condition can be identified over time. In addition, CDW may provide an active link to external clinical knowledge source where the user can learn more details about a procedure or symptoms reported by a radiologist. Typically, user inputs cause the CDW to expand outward from a compact root concepts ring or arc to display information in the form of one or more outwardly expanding rings or arcs. The outermost ring, arc, or timeline presents medical reports for the patient.

More particularly, text of medical reports of a patient are analyzed, e.g. using regular expressions and/or natural language processing (NLP), to annotate text segments with clinical concepts from a medical ontology. This provides a standardized labeling of the medical reports with annotations made to specific text segments. In the CDW, the medical reports are represented by icons (e.g. arc segments of a ring or arc, or blocks of a linear timeline) that are labeled the relevant text segment that is annotated with the clinical concept.

The proposed system provides a tool for presenting information on a patient from freeform medical reports in an accessible fashion. A clinical concept annotator annotates freeform medical reports based on regular expressions, natural language processing (NLP) or other analysis. The annotations are framed in a standard medical ontology such as the Systematized Nomenclature of Medicine (SNOMED®) ontology or the RadLex® radiology ontology. A rule engine links reports to clinical concepts based on the annotations.

The linked information database for the patient thus created is displayed using an interactive structure. In this interactive structure, the basic clinical concept categories (CCC's) form the hub or root of the wheel (e.g. the CDW). By way of non-limiting illustration, in one example the CCCs include: "clinical findings"; "symptoms"; "diagnoses"; "medical procedures"; and "body structures", which accord with some broad SNOMED CT categories. Upon user selection of a CCC, the wheel expands outward from the hub by displaying child categories, e.g. clinical concepts falling under the selected category. There may be one or more such expansions; the final outermost level is the report timeline, in which freeform medical reports relating to the chosen category are listed in time order, with each medical report represented by a text block displaying a text snippet from the medical report relating to the chosen category. By clicking on such a text block the entire freeform medical report can be brought up, e.g. in a pop-up window. The illustrative report timeline may be formed in a ring fashion to wrap partway around the wheel for compactness.

The approaches described herein may also provide a visualization tool to explore clinical concepts stored in a healthcare informatics system (HIS) such as Electronic Medical Record (EMR), Radiology Information System (RIS), or so forth. Radiologists and referring physicians can interactively explore clinical concepts without interrupting their regular workflow. Advantageously, this allows for the exploration of clinical concepts in different levels of detail depending on the need and interest of the user. For example, a radiologist can first look into a body structure section to learn the region affected by a metastasized sarcoma, then open more information on a specific body structure such as chest to see how sarcoma are described in the radiology reports, and finally choose a specific radiology report to view in more detail. The CDW minimizes the time expended to learn patient information in different systems across the HIS. The CDW may also associate clinical concepts to text segments using a medical ontology such as RadLex® or SNOMED, which provides additional information about the clinical concepts organized by the tool.

The CDW provides an interactive way to explore patient information. Using textual annotation tools such as Natural Language Processing (NLP), regular expressions, and/or deep machine learning, the CDW creates a compact and intelligent view of the freeform textual data spread over different healthcare silos (e.g. databases), thus providing a single interface point integrating these diverse data sources. Radiologists can review the most relevant patient events without interrupting their workflow. The CDW may also provide links to external clinical knowledge sources to facilitate medical reference during the discovery process.

Figure 1:
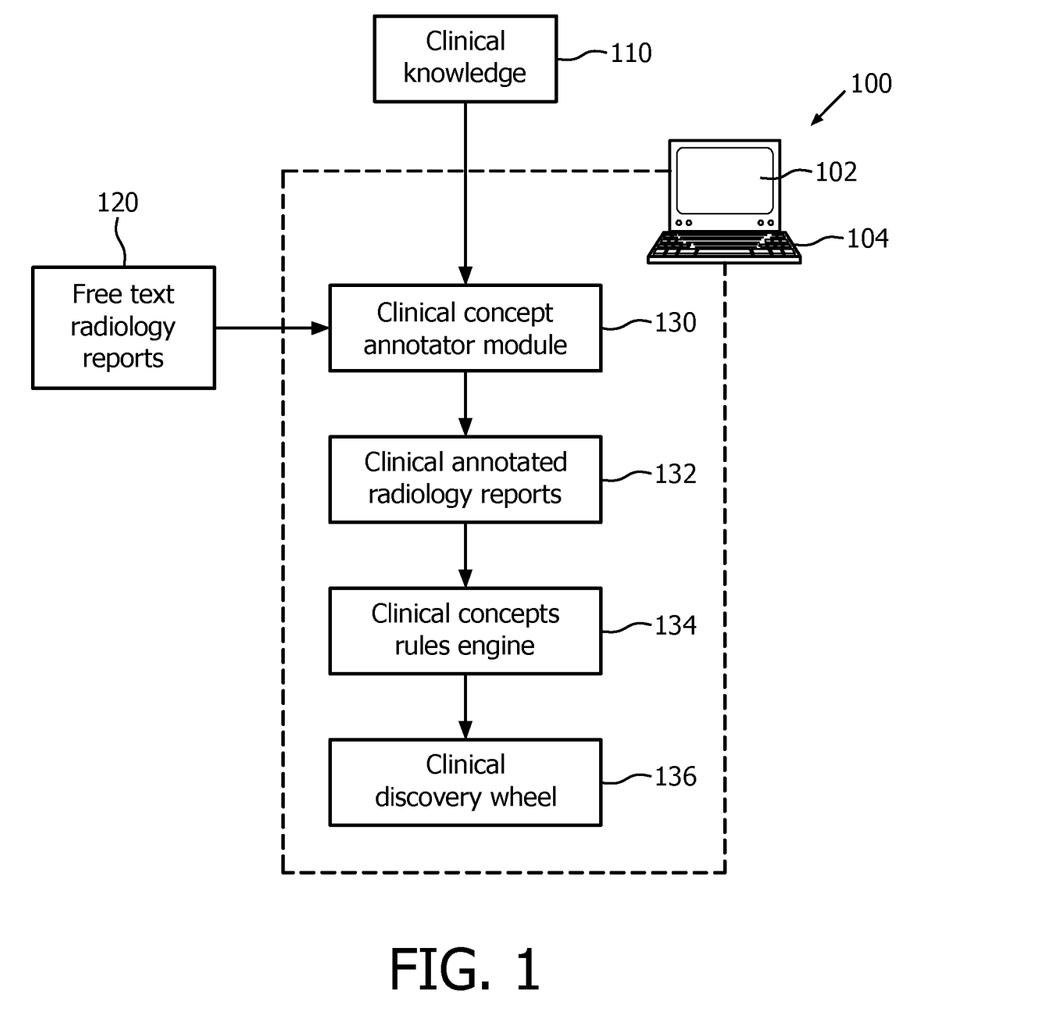
FIG. 1 diagrammatically shows a system to explore clinical concepts.

FIG. 1 diagrammatically shows a system to explore clinical concepts. With reference thereto, computer 100 includes a display 102 and illustrative keyboard 104. More generally, the user input device 104 may include a keyboard, a mouse, trackball or other pointing device, a touchscreen display component of the display 102, or so forth. Clinical knowledge 110 includes a database or databases that store medical information (e.g., medical ontologies such as SNOMED and RadLex®). Clinical knowledge 110 may further include general treatment information for conditions, as well as patient history information. Free text radiology reports (or other medical reports) 120 are generated by a radiologist or other medical professional in compliance with orders from a referring physician or other user. Clinical concept annotator module 130 uses Natural Language Processing (NLP), Regular Expression (Regex) analysis, keyword identification, extracted ICD-9 codes or other medical classification codes appearing in report text, or so forth to annotate specific text segments of the freeform text of the medical reports 120 with clinical concepts, for example using medical ontologies (e.g., SNOMED and RadLex®) to identify standard terms associated with various such concepts. Keywords or medical codes provide an efficient semantic analysis tool, but could produce misleading results due to lack of context. Regular expressions can provide some context (e.g. identifying a textual phrase positively or negatively linking "tumor" and "metastasiz . . . "). NLP provides fuller contextual information by grammatically parsing textual sentences to provide richer information on interrelationships of medical terms. Terms and term combinations extracted by such techniques are compared with a medical ontology to identify the clinical concepts implied by the text segments. The clinical concept annotator module 130 may parse and annotate clinical concepts in the healthcare information system (e.g., radiology report from the RIS or patient history from the EMR). This produces annotated radiology reports 132 (or, more generally, annotated medical reports, e.g. radiology reports, specialist examination reports, histopathology laboratory reports or other laboratory test reports, or so forth). In some embodiments, each clinical concept may be weighted in accordance with their frequency and relevance for the patient history.

Figure 2:
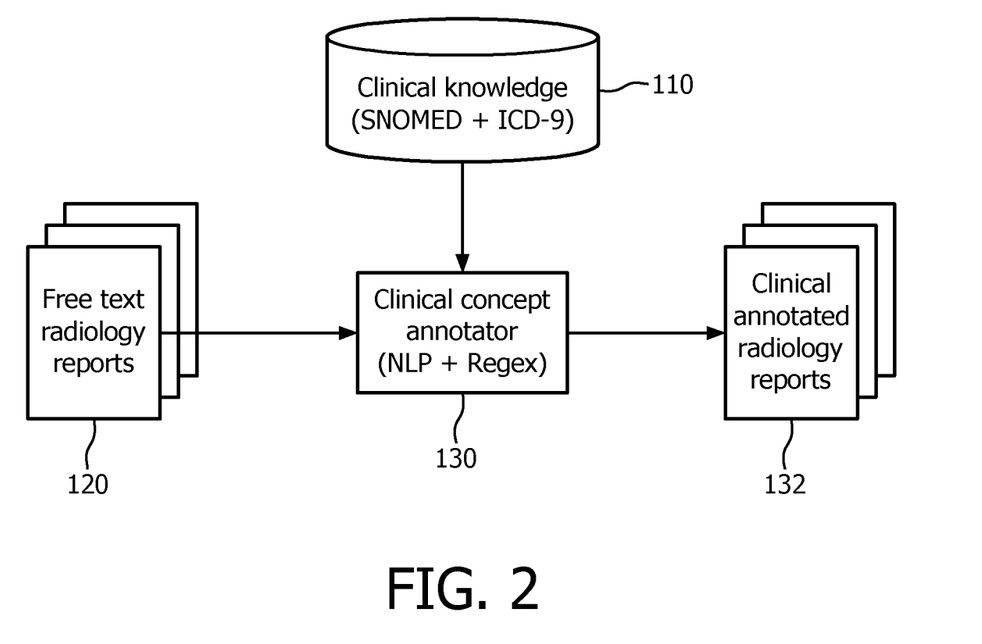
FIG. 2 graphically displays a clinical concept annotator.

FIG. 2 provides a graphical illustration of the free text radiology reports 120, the clinical concept annotator module 130, the clinical knowledge 110, and clinical annotated radiology reports 132 discussed above.

Returning to FIG. 1, a clinical concepts rule engine 134 creates rules to guide the exploration of clinical concepts from healthcare information system. These rules associate clinical concepts in two different levels: report level and patient level. In the report level, clinical concepts annotated by the annotator module 130 are clustered according to categories from clinical medical ontologies. For example, the clinical concepts could be clustered according with Systematized Nomenclature of Medicine—Clinical Terms (SNOMED CT) categories such as clinical findings, symptoms, diagnoses, procedures or body structures. The categories are called clinical concepts categories (CCC).

The patient level of rules considers a longitudinal view of the clinical annotated radiology reports 132 from radiology reports and EMR data for a given patient. These context-sensitive rules link between clinical concepts in different radiology reports, and thus provide a comprehensive analysis of all the references of clinical concepts in all radiology report for a given patient. The context-sensitive rules associated with clinical heuristics provide the ability to learn how a disease or clinical finding evolves over the history of a patient by identifying text segments in medical reports generated for the patient over the course of treatment that pertain to the disease or clinical finding as labeled by the annotator 130. Clinical concepts rule engine 134 generates linkage information that is used by a clinical discovery wheel (CDW) graphical user interface (GUI) 136 in navigating the textual information contained in the medical reports 120.

Figure 3:
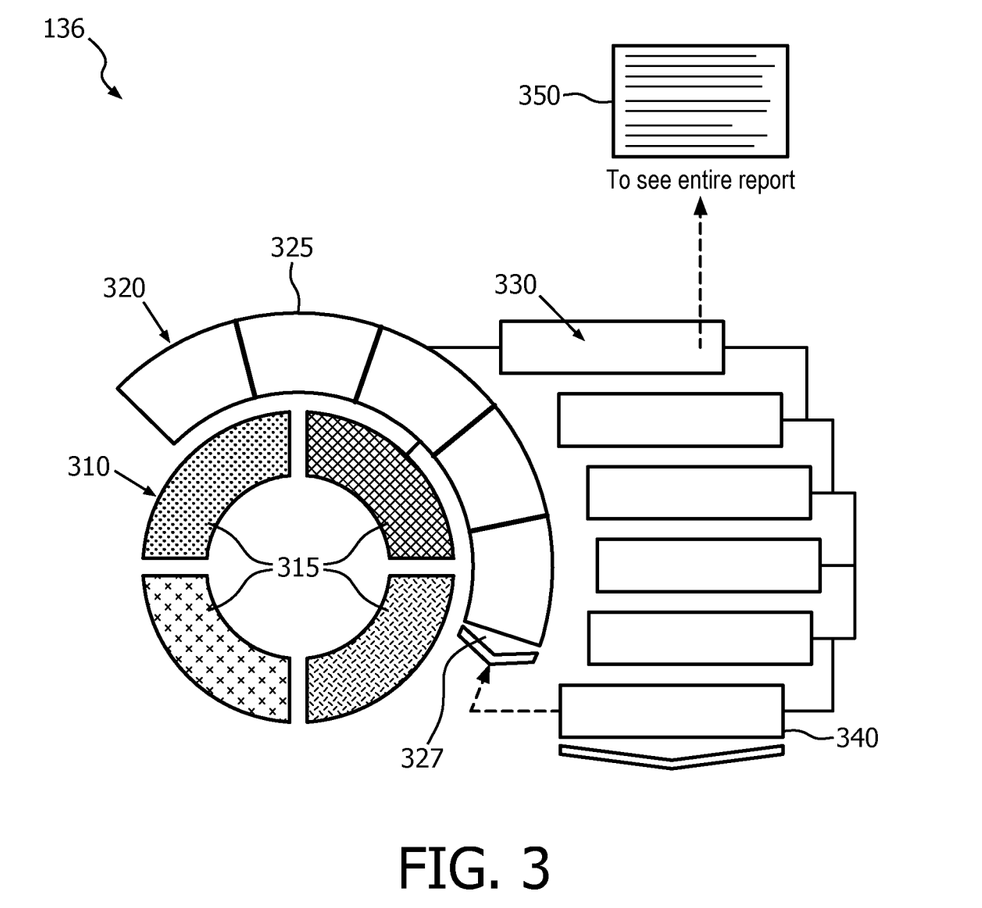
FIG. 3 shows an exemplary illustration of a clinical discovery wheel interface.
Figure 4A:
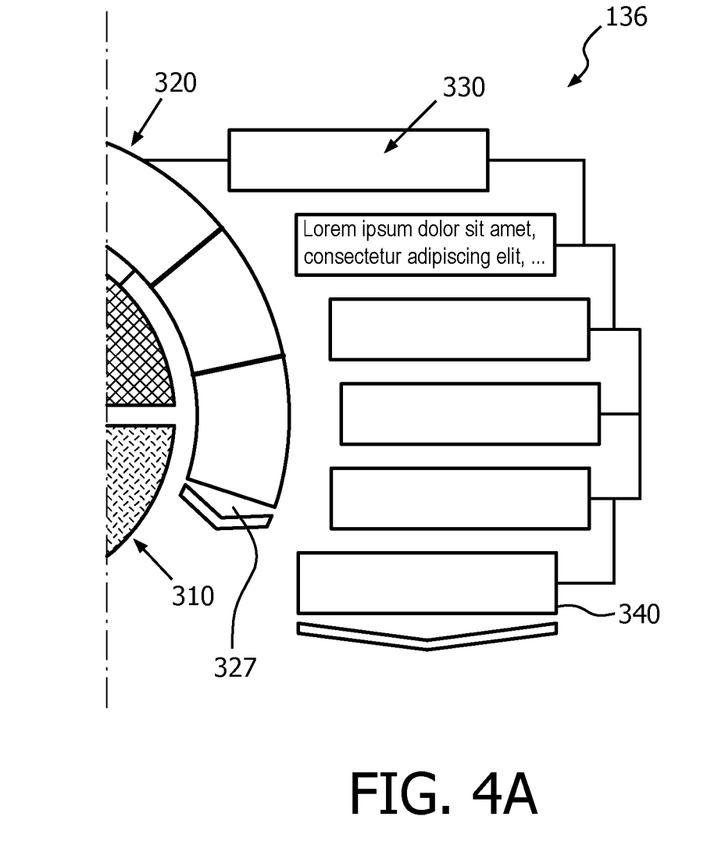
FIG. 4a shows another exemplary illustration of a clinical discovery wheel interface.
Figure 4B:
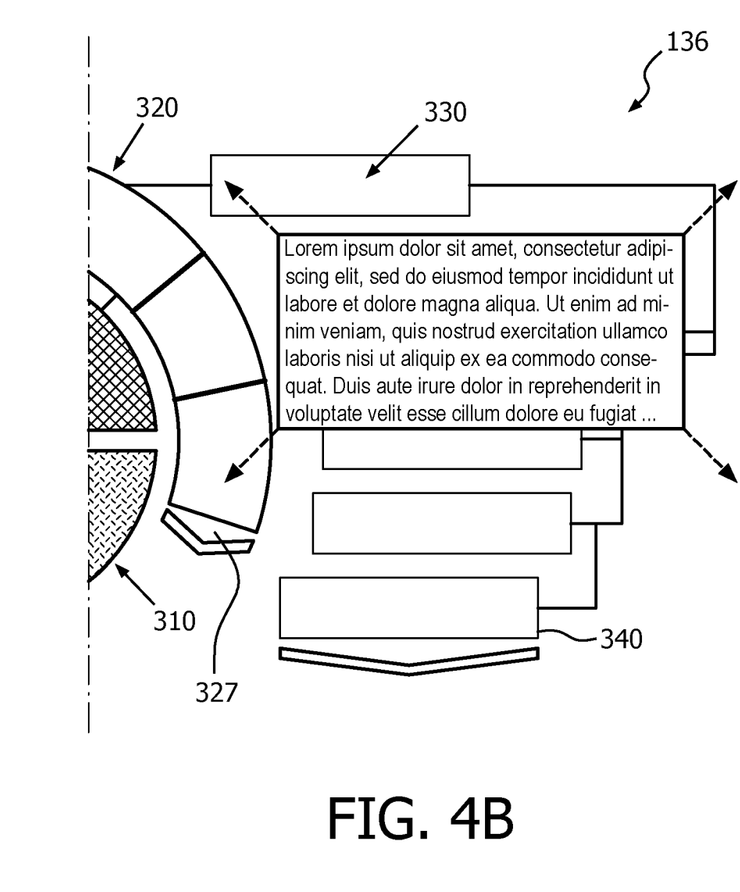
FIG. 4b shows another exemplary illustration of a clinical discovery wheel interface.

With reference to FIGS. 3, 4a and 4b, the CDW 136 provides an interactive graphic user interface based on concentric rings or arcs that are shown or hidden by user interaction. Starting from a root concepts ring or arc 310 (a full ring in the illustrative example) containing icons in the form of arc segments 315 representing clinical concepts categories (CCC) obtained from patient heath information and using the two previous described modules, the user can select a CCC 315 from the root concepts ring 310, and in response a new ring or arc 320 is built and displayed around (i.e. at least partially encircling) the root concepts circle 310. The user selection of the user-selected clinical concept category uses the at least one user input device 104, and may for example be selected by clicking, double clicking, or mouseovering one of the CCCs 315. This newly created ring or arc 320 is called children concept ring or arc (CCR) 320 (displayed as an arc in the illustrative example) and contains arc segments 325 representing clinical concepts associated with the user-selected selected CCC 315. Various user inputs may have varying effects: for example, in one embodiment the difference between the clicking and mouseover may be that clicking shows the children concepts until a later command is received; whereas, the mouseovering shows the children concepts only when the mouse is over the CCCs. In addition, the illustrative CCR 320 includes an end terminating in an arrow icon 327 (i.e. scroll icon 327) via which the user may rotate the CCR 320 to view additional clinical concepts under the user-selected CCC.

The CCR 320 at least partially encircles the root concepts ring or arc 310. This provides a compact display. Other similar compact display formats are also contemplated, such as an arrangement in which the CCCs are displayed as icons in a central square root region, and the child clinical concepts built by user selection of a CCC are displayed as an added outer region that expands outwardly from the central square root region containing the CCC icons and at least partially surrounds it.

By clicking or mouseovering a CCR 320, the user may create a new concentric ring or arc named grandchildren concept ring (GCR) 330 or a straight or arced timeline 330. The illustrative timeline 330 is an arced timeline that partially encircles the CCR 320, again enhancing compactness. The GCR 330 includes icons representing clinical (sub-) concepts or, in the outermost layer, representing individual medical reports or other at least partially text-based information sources. Each icon (e.g. block or arc segment) of the ring-fashion-timeline 330 includes (at least a portion of) a text segment of the medical report that is annotated with the user-selected clinical concept. This enables the user to immediately assess the reason why the medical report has been deemed relevant to the user-selected clinical concept. To provide context (and space permitting), the displayed text segment may optionally include a few words that precede and succeed the annotated text segment of the medical report. If space is limited, a scroll icon 340 may again be provided to scroll through the blocks of the timeline 330.

If the user wishes to see the entire medical report, this may be done by selecting the icon representing the medical report, which brings up a pop-up window 350 containing the entire medical report. Alternatively, this operation may open a separate program (e.g. a text editor or report browsing program) with the medical report loaded. The presented summary 340 may contain a part of the report that includes the children concept.

Figure 5:
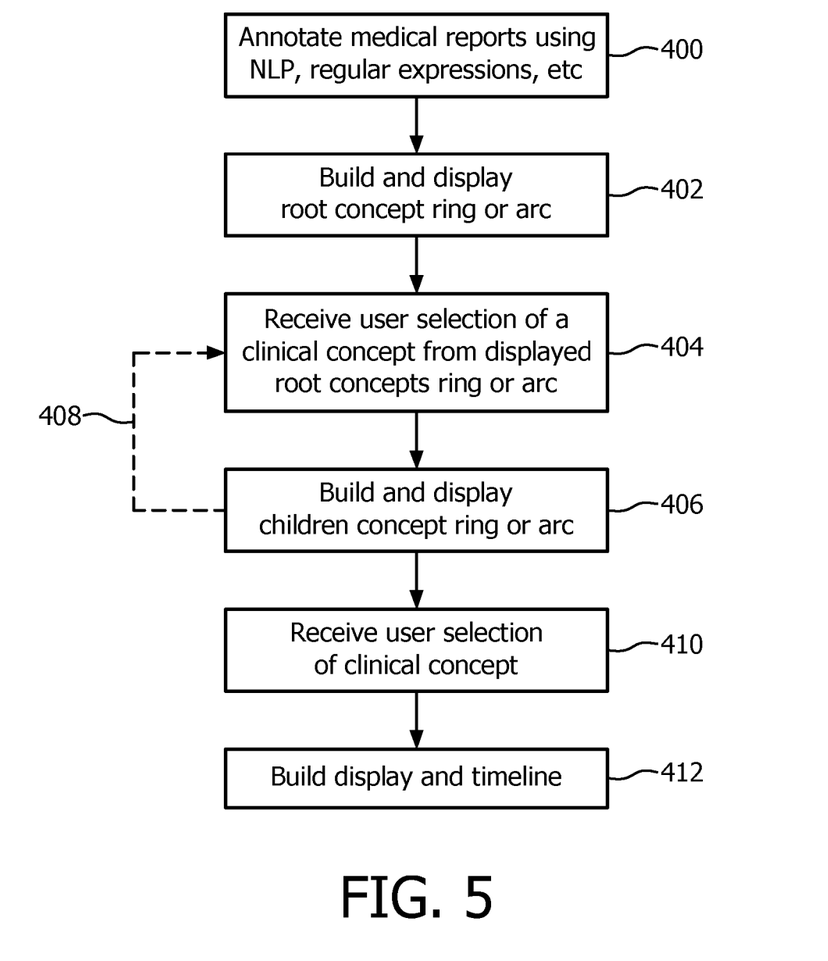
FIG. 5 illustrates a method of navigating medical report information using a CDW system.

With reference to FIG. 5, a method of navigating medical report information using the CDW system of FIG. 1 is described. In an operation 400, medical reports 120 are annotated by the annotator module 130 by associating clinical concepts with text segments of the medical reports. In an operation 402, the root concepts circle ring or arc 310 is built and displayed on the display device 102. The root concepts circle ring or arc 310 includes arc segments 315 representing clinical concept categories (CCC's). Then, in an operation 404 performed by the user operating the user input device 104 on the displayed root concepts ring or arc, a user selection is received of an arc segment representing a clinical concept category. The user operation identifies a user-selected clinical concept category. In an operation 406, a children concept ring or arc 320 is then built and displayed, which expands the user-selected clinical concept category and at least partially encircles the root concepts ring or arc. The children concept ring or arc 320 includes arc segments 325 representing clinical concepts of the user-selected clinical concept category.

It will be appreciated that the operations 404, 406 may optionally be repeated one or more times to create "grandchildren", "great-grandchildren", etc clinical concept rings or arcs, each encircling the previous ring or arc and each optionally including features such as the scroll icon 327. This is indicated in FIG. 5 by loop arrow 408.

With continuing reference to FIG. 5, in an operation 410 user input is received via the user input device 104 operating on the displayed children (or grandchildren, or great-grandchildren, etc) concept ring or arc to make a user selection of an arc segment representing a clinical concept. This identifies a user-selected clinical concept for which relevant medical reports are to be viewed. In an operation 412, the timeline 330 is built and displayed adjacent (and optionally at least partially encircling or surrounding) the children concept ring or arc from which it expands. The timeline 330 comprises arc segments or blocks representing medical reports annotated with the user-selected clinical concept.

The wheel shaped components of CDW 136 result in a more compact design displayed on a medical display device. This more compact design results in lower burden on any processors and memory in the medical display device; thus, the compact design of CDW 136 improves the technical functioning of the medical display device.

It will be further appreciated that the techniques disclosed herein may be embodied by a non-transitory storage medium storing instructions readable and executable by an electronic data processing device (such as the computer 100) to perform the disclosed techniques. Such a non-transitory storage medium may comprise a hard drive or other magnetic storage medium, an optical disk or other optical storage medium, a cloud-based storage medium such as a RAID disk array, flash memory or other non-volatile electronic storage medium, or so forth.

Of course, modifications and alterations will occur to others upon reading and understanding the preceding description. It is intended that the invention be construed as including all such modifications and alterations insofar as they come within the scope of the appended claims or the equivalents thereof.

The invention claimed is:

1. A non-transitory storage medium storing instructions readable and executable by an electronic device to perform a method for navigating clinical information using a wheel structure in a graphical user interface, the non-transitory storage medium storing:
   a medical ontology of clinical concepts;
   instructions for annotating medical reports by associating clinical concepts with text segments of the medical reports;
   instructions for displaying, on a graphical user interface (GUI), text segments of the medical reports with natural language processing (NLP) and regular expressions to associate the text segments with clinical concepts clustered according to categories from the medical ontology;
   instructions for building and displaying, on the GUI, a wheel structure initially including a root region structured as a root concepts ring, wherein each arc segment of the root concepts ring corresponds to a respective clinical concept category of a plurality of clinical concept categories, wherein the plurality of clinical concept categories comprise clinical findings, symptoms, diagnoses, medical procedures, and body structures, wherein the root region comprises a square region;
   instructions for receiving, via a user input device operating on the displayed root concepts ring or arc, a user selection of an arc segment representing a clinical concept category whereby a user-selected clinical concept category is identified;
   instructions for, in response to the user selection of the arc segment representing a clinical concept category whereby the user-selected clinical concept category is identified, expanding a size of the wheel structure on the GUI by building and displaying a children concept ring or arc expanding the user-selected clinical concept category and at least partially encircling the root concepts ring or arc, the children concept ring or arc including arc segments representing clinical concepts of the user-selected clinical concept category, the children concept ring or arc not being displayed to the user until the user provides the user selection of the arc segment representing the clinical concept category, the children concept ring o r arc adjacent to but not in direct contact with the root concepts ring or arc;
   instructions for receiving via the user input device operating on the displayed children concept ring or arc a user selection of an arc segment representing a clinical concept whereby a user-selected clinical concept is identified; and
   instructions for building and displaying, adjacent the children concept ring or arc, an interactive timeline comprising arc segments or blocks representing medical reports annotated with the user-selected clinical concept, wherein the interactive timeline corresponds to a course of treatment of a particular disease;
   wherein the arc segments represent medical reports annotated with the user-selected clinical concept that display at least a portion of a text segment of the medical report that is annotated with the user-selected clinical concept.

2. The non-transitory storage medium of claim 1, wherein the interactive timeline is displayed as a timeline ring or arc at least partially encircling the children concept ring or arc.

3. The non-transitory storage medium of claim 1, further comprising:
   instructions for receiving, via the user input device operating on the interactive timeline, a user selection of an arc segment or block representing a medical report whereby a user-selected medical report is identified; and
   instructions for displaying the user-selected medical report in a pop-up window.

4. The non-transitory storage medium of claim 1, wherein the medical reports include radiology reports.

5. The non-transitory storage medium of claim 1, further comprising, after building and displaying the children concept ring or arc:
   instructions for expanding the user-selected clinical concept category, receiving via the user input device operating on the displayed children concept ring or arc a user selection of an arc segment of the children concept ring or arc, whereby a user-selected intermediate clinical concept is identified for further expansion; and instructions for building and displaying a children concept ring or arc expanding the user-selected intermediate clinical concept and at least partially encircling the previously displayed children concept ring or arc and including arc segments representing clinical concepts which are sub-concepts of the user-selected intermediate clinical concept.

6. The non-transitory storage medium of claim 1, further comprising:

instructions for displaying the children concept ring or arc as an arc with an end terminating in a scroll icon; and in response to user activation of the scroll icon via the user input device, instructions for scrolling the children concept arc to display at least one additional arc segment representing at least one additional clinical concept of the user-selected clinical concept category.

7. The non-transitory storage medium of claim 1, wherein the medical ontology of clinical concepts comprises the Systematized Nomenclature of Medicine-Clinical Terms (SNOMED CT) ontology or the RadLex ontology.

8. An electronic device configured to display medical information including building a root region and outwardly expanding regions, the electronic device comprising:

a user input device; and an electronic processor programmed to:

annotate medical reports by associating clinical concepts with text segments of the medical reports;

build and display, on a graphical user interface (GUI), text segments of the medical reports with natural language processing (NLP) and regular expressions to associate the text segments with clinical concepts clustered according to categories from a medical ontology of clinical concepts;

build and display, on the GUI, a wheel structure initially including a root region structured as a ring including icons representing a plurality of clinical concept categories wherein each arc segment of the ring corresponds to a respective clinical concept category of the plurality of clinical concept categories, and the plurality of clinical concept categories comprise clinical findings, symptoms, diagnoses, medical procedures, and body structures, wherein the root region comprises a square region;

receive, via the user input device, a user selection of an arc segment representing a clinical concept category whereby a user-selected clinical concept category is identified;

expanding, on the GUI in response to the user selection of the arc segment representing a clinical concept category whereby the user-selected clinical concept category is identified, expanding a size of the wheel structure on the GUI by building and displaying a children concept ring or arc expanding the user-selected clinical concept category and at least partially encircling the root concepts ring or arc, the children concept ring or arc including arc segments representing clinical concepts of the user-selected clinical concept category, the children concept ring or arc not being displayed to the user until the user provides the user selection of the arc segment representing the clinical concept category, the children concept ring or arc adjacent to but not in direct contact with the root concepts ring or arc;

receive, via the user input device operating on the displayed children concept ring or arc a user selection of an arc segment representing a clinical concept whereby a user-selected clinical concept is identified; and build and display, on the GUI, an interactive timeline including icons representing clinical concepts or medical reports of the user-selected clinical concept selected via the user input device from the first outwardly expanding region, wherein the icons correspond to a course of treatment of a particular disease and text segments of the medical reports are displayed with natural language processing (NLP) and regular expressions to associate the text segments with clinical concepts clustered according to categories from Systematized Nomenclature of Medicine-Clinical Terms (SNOMED CT) or RadLex categories;

wherein the arc segments further represent medical reports annotated with the user-selected clinical concept that display at least a portion of a text segment of the medical report that is annotated with the user-selected clinical concept.

9. The electronic device of claim 8, wherein the interactive timeline is a straight, vertical timeline of icons representing medical reports.

10. The electronic device of claim 8, wherein the interactive timeline is a curved timeline of icons representing medical reports, the curved timeline at least partially surrounding the first outwardly expanding region.

11. The electronic device of claim 8, wherein the interactive timeline includes an icon representing a medical report by displaying in the icon a text segment of the medical reort that is annoted with the user-selected clinical concept.

12. The electronic device of claim 8, wherein the first outwardly expanding region is ring or arc region.

13. An electronic device configured to present content of medical reports of a patient, the electronic device comprising:

a user input device; and an electronic processor programmed to:

annotate medical reports by associating clinical concepts with text segments of the medical reports;

build and display. on a graphical user interface (GUI), text segments of the medical reports with natural language processing (NLP) and regular expressions to associate the text segments with clinical concepts clustered according to categories from a medical ontology of clinical concepts;

build and display, on the GUI, a wheel structure initially including a root concepts ring or arc including icons representing a plurality of clinical concept categories wherein each arc segment of the root concepts ring corresponds to a respective clinical concept category of the plurality of clinical concept categories, and the plurality of clinical concept categories comprise clinical findings, symptoms, diagnoses, medical procedures, and body structures, wherein the root region comprises a square region;

receive, via a user input device operating on the displayed root concepts ring or arc, a user selection of an arc segment representing a clinical concept category whereby a user-selected clinical concept category is identified;

in response to the user selection identifying the user-selected clinical concept category, expanding the root concepts ring or arc by building and displaying, on the GUI, an outwardly expanding ring or arc at least partially encircling the root region and including icons representing clinical concepts of the user-selected clinical concept category, the outwardly expanding ring or arc not being displayed until after the user selection identifying the user-selected clinical concept category, the outwardly expanding ring or arc adjacent to but not in direct contact with the root concepts ring or arc;

receive a selection of a user-selected clinical concept via a user input device operating on the displayed outwardly expanding ring or arc; and in response to the user selection of the user-selected clinical concept, building and displaying, on the GUI and adjacent the outwardly expanding ring or arc, a timeline comprising arc segments or blocks, each arc segment or block containing at least one text segment from the medical reports of the patient that is annotated with the user-selected clinical concept, the timeline not being displayed until after the user selection of the user-selected clinical concept;

wherein the arc segments further represent medical reports annotated with the user-selected clinical concept that display at least a portion of a text segment of the medical report that is annotated with the user-selected clinical concept.

\* \* \* \* \*